United States Patent [19]

Jahn et al.

[11] Patent Number: 5,728,578
[45] Date of Patent: Mar. 17, 1998

[54] PEPTIDE OF THE STRUCTURAL PHOSPHOPROTEIN (PP 150) OF HUMAN CYTOMEGALOVIRUS, AND DNA ENCODING SAID PEPTIDE

[75] Inventors: Gerhard Jahn, Neunkirchen; Birgit-Christine Scholl, Uttenreuth; Michael Bröker, Marburg; Michael Mach, Erlangen; Bernhard Fleckenstein, Schlaifhausen; Bernd Traupe, Hausen, all of Germany

[73] Assignee: Behring Diagnostics GmbH, Marburg, Germany

[21] Appl. No.: 159,710

[22] Filed: Dec. 1, 1993

Related U.S. Application Data

[63] Continuation of Ser. No. 35,891, Mar. 23, 1993, abandoned, which is a continuation of Ser. No. 890,867, Jun. 1, 1992, abandoned, which is a division of Ser. No. 726,164, Jul. 2, 1991, abandoned, which is a continuation of Ser. No. 471,072, Jan. 29, 1990, abandoned, which is a continuation of Ser. No. 60,159, Jun. 10, 1987, abandoned.

[30] Foreign Application Priority Data

Jun. 12, 1986 [DE] Germany ............ 36 19 718.1

[51] Int. Cl.$^6$ ............ C12N 15/70; C12N 15/38; C07K 14/045
[52] U.S. Cl. ............ 435/320.1; 435/69.3; 424/186.1; 424/230.1; 530/324; 530/352; 536/23.72; 935/12
[58] Field of Search ............ 424/186.1, 230.1; 935/12; 435/69.3, 320.1; 536/23.72; 530/352, 324

[56] References Cited

U.S. PATENT DOCUMENTS

| | | |
|---|---|---|
| 4,554,101 | 11/1985 | Hopp . |
| 4,554,159 | 11/1985 | Roizman et al. . |
| 4,689,225 | 8/1987 | Perrira . |
| 4,716,104 | 12/1987 | Harris et al. . |
| 4,743,562 | 5/1988 | Rasmussen et al. . |
| 4,762,780 | 8/1988 | Spector et al. . |
| 4,769,331 | 9/1988 | Roizman et al. . |
| 4,808,518 | 2/1989 | Dorsett et al. . |

OTHER PUBLICATIONS

Perieira et al. Infection and Immunity 39(1):100–108 Jan. 1983.

Young and Davis PNAS 80:1194–1198 Mar. 1983.

Cremer et al., Chem. Abs. 102:183542V 1985.

Rassmussen et al. J. Virol. 55(2):274–280 1985.

Rassmussen et al. Virol 145:186–190 1985.

Landini et al. Chem. Abs. 104:86615e 1986.

Rassmussen et al. Chem. Abs. 103:86154h 1985.

Rassmussen et al. Chem. Abs. 103:103078f 1985.

Nowak et al. Chem. Abs. 101:18312s 1984.

Broker et al. Gene Anol. Techn. 3:53–57 1986.

Landini et al. J. Med. Virology 17(4):303–311 1985.

Gibco BRL Catalogue; see p. 358, 1990.

Lazar et al. Molecular and Cellular Biology 8(3):1247–52, Mar. 1988.

Burgess et al. The Journal of Cell Biology 111:2129–2138, Nov. 1990.

Cremer et al. Antibody Response to Cytomegalavirus Polypeptides Captured by Monoclonal Antibodies on the Solid Phase in Enzyme Immunoassays J. Clin Microbiol 21(4) 517–21 1985.

Gibson Protein Counterparts of Human and Simian Cytomegaloviruses Virology 128 391–406 1983.

Tamashiro et al. Construction of a Cloned Library of the Ecort Fragments from the Human Cytomegalovirus Genome (Strain AD169). Virology 1982 547–557.

Fleckenstein et al. Cloning of the Complete Human Cytomegalovirus Genome in Cosmids. Gene 1982 39–46.

Tamashiro et al. Structure of a Heterogeneous L–S Junction Region of Human Cytomegalovirus Strain AD169 DNA. J. of Virology 52(2) 541–48 1984.

Jahn et al., J. Gen. Virol. 68:1327–37 (1987).

Jahn et al., Chem. Abs. 107:37701h (1987).

Jahn et al., J. Virol. 61(5):1358–67 (1987).

Jahn et al., Chem. Abs. 107:110137k (1987).

Benko et al., Chem. Abs. 108:217994k (1988).

M.G. Davis et al., Chem. Abs. 101:205291w (1984).

M.G. Davis et al., Chem. Abs. 103:207739p (1985).

B. Rueger et al., Chem. Abs. 106:169906t (1987).

Benko et al., Proc. Natl. Acad. Sci. USA 85:2573–77 (1988).

*Primary Examiner*—Anthony C. Caputa
*Attorney, Agent, or Firm*—Finnegan, Henderson, Farabow, Garrett & Dunner, L.L.P.

[57] ABSTRACT

The phosphorylated structural protein of molecular weight about 150 kd (pp 150) of human cytomegalovirus (HCMV) is highly immunogenic and is reliably recognised by human antisera. This protein can, after assignment and sequencing of the gene, be prepared, in whole or in immunogenic sections, by gene manipulation. Proteins of this type are suitable as reagents, for example in an ELISA, and as constituents of vaccines.

3 Claims, 2 Drawing Sheets

FIG. 1-1

Eco RI
```
GAATTCGATA CGGACGTGCG CCACGATGCC GAGATCGTGG AACGCGCGCT  50

CGTAAGCGCG GTCATTCTGG CCAAGATGTC GGTGCGCGAG ACGCTGGTCA 100

CAGCCATCGG CCAGACGGAA CCCATCGCCT TGTGCACCT CAAGGATACG 150

GAGGTGCAGC GCATTGAAGA AAACCTGGAG GGTGTGCGCC GTAACATGTT 200

CTGCGTGAAA CCGCTCGACC TTAACCTGGA CCGGCACGCC AACACGGCGC 250

TGGTCAACGC CGTCAACAAG CTCGTGTACA CGGGCCGTCT CATCATGAAC 300

GTGCGCAGGT CTTGGGAGGA GCTGGAGCGC AAATGTCTGG CGCGCATTCA 350

GGAGCGCTGC AAGCTGCTGG TCAAGGAGCT GCGCATGTGC CTTTCCTTTG 400

ATTCCAACTA CTGTCGCAAT ATCCTCAAGC ACGCCGTGGA AAACGGCGAC 450

TCGGCCGACA CGCTGTTGGA GCTGCTCATC GAGGACTTTG ATATCTACGT 500

GGACAGCTTC CCACAGTCGG CGCACACGTT TTTGGGCGCG CGCTCGCCGT 550

CGTTGGAGTT TGACGATGAC GCCAATCTCC TCTCGCTCGG CGGCGGTTCG 600

GCCTTCTCGT CGGTACCCAA GAAACATGTC CCCACGCAGC CGCTGGACGG 650

CTGGAGCTGG ATCGCCAGTC CCTGGAAGGG ACACAAACCG TTCCGCTTCG 700

AGGCCCATGG TTCTCTGGCA CCGGCCGCCG AAGCCCACGC TGCCCGTTCG 750

GCGGCCGTCG GCTATTACGA CGAAGAGGAA AAGCGTCGCG AGCGGCAGAA 800

ACGGGTGGAC GACGAGGTGG TGCAGCGTGA GAAACAGCAG CTGAAGGCTT 850

GGGAGGAGAG GCAGCAGAAC CTGCAGCAAC GTCAGCAGCA ACCACCGCCC 900

CCGGCACGTA AACCGAGCGC CTCCCGGAGG CTCTTTGGCT CCAGTGCCGA 950

TGAGGACGAC GACGATGATG ATGACGAGAA AAACATCTTT ACGCCCATCA 1000
```

FIG. 1-2

```
AGAAACCGGG AACTAGCGGC AAGGGCGCCG CTAGTGGTGG CGGTGTTTCC 1050

AGCATTTTCA GCGGCCTGTT ATCCTCGGGC AGTCAGAAAC CGACCAGCGG 1100

TCCCTTGAAC ATCCCGCAAC AACAACAGCG TCACGCGGCT TTCAGTCTCG 1150

TCTCCCCGCA GGTGACCAAG GCCAGCCCGG GAAGGGTCCG TCGGGACAGC 1200

GCGTGGGACG TGAGGCCGCT CACGGAGACC AGAGGGGATC TTTTCTCGGG 1250
                                                  XhoII
CGACGAGGAT TCCGACAGCT CGGATGGCTA TCCCCCCAAC CGTCAAGATC 1300

CGCGTTTCAC CGACACGCTG GTGGACATCA CGGATACCGA GACGAGCGCC 1350

AAACCGCCCG TCACCACCGC GTACAAGTTC GAGCAACCGA CGTTGACGTT 1400

CGGCGCCGGA GTTAACGTTC CTGCTGGCGC CGGCGCTGCC ATCCTCACGC 1450

CGACGCCTGT CAATCCTTCC ACGGCCCCCG CTCCGGCCCC GACACCTACC 1500

TTCGCGGGTA CCCAAACCCC GGTCAACGGT AACTCGCCCT GGGCTCCGAC 1550

GGCGCCGTTG CCCGGGGATA TGAACCCCGC CAACTGGCCG CGCGAACGCG 1600

CGTGGGCCCT CAAGAATCCT CACCTGGCTT ACAATCCCTT CAGGATGCCT 1650

ACGACTTCCA CGGCTTCTCA AAACACCGTG TCCACCACCC CTCGGAGGCC 1700

GTCGACTCCA CGCGCCGCGG TGACACAAAC AGCGTCTCGG GACGCCGCTG 1750
                                          PstI
ATGAGGTTTG GGCTTTAAGG GACCAAACTG CAG                 1783
```

PEPTIDE OF THE STRUCTURAL PHOSPHOPROTEIN (PP 150) OF HUMAN CYTOMEGALOVIRUS, AND DNA ENCODING SAID PEPTIDE

This application is a continuation of application Ser. No. 08/035,891 filed Mar. 23, 1993, now abandoned, which is a continuation of application Ser. No. 07/890,867, filed Jun. 1, 1992, now abandoned, which is a division of application Ser. No. 07/726,164, filed Jul. 2, 1991, now abandoned, which is a continuation of application Ser. No. 07/471,072, filed Jan. 29, 1990, now abandoned, which is a continuation of application Ser. No. 07/060,159, filed Jun. 10, 1987 now abandoned.

A phosphorylated structural protein of about 150 kd (pp 150) is a constituent of purified virion particles. According to W. Gibson, Virology 128 (1983) 391–406, it is a constituent of the matrix. It is suitable as a diagnostic aid because of its strongly immunogenic properties.

The invention relates to pp 150 and immunogenic parts of this protein, to their preparation by gene manipulation and their use as an immunological reagent, for example in an ELISA. Preferred embodiments of the invention in their various aspects are explained in detail hereinafter and defined in the patent claims.

BRIEF DESCRIPTION OF THE DRAWING

FIG. 1 shows the cDNA of clone BB 8.

It has been found that it is possible with a monospecific rabbit antiserum against pp 150 to identify the desired clones from a HCMV cDNA gene bank. For this purpose, a sample of the entire viral protein was subjected to preparative SDS polyacrylamide gel electrophoresis, and the individual protein bands were visualized using the dye-stuff $^R$Coomassie (ICI) brilliant blue. The protein with the molecular weight of 150 kd was cut out, extracted and used for immunizing rabbits. The antiserum which was obtained reacted with the 150 kd protein in a Western blot test. This serum was used to screen the cDNA gene bank.

To set up the gene bank, human preputial fibroblast cells were infected with HCMV, strain Ad 169, and, 96 to 120 hours after the infection, the poly(A)$^+$ RNA was isolated and converted into dsDNA and the latter was, without size fractionation, inserted into the commercially available phage expression vector λgt11. For this purpose, the vector was cleaved with EcoRI and treated with alkaline phosphatase (from calf intestine) to suppress intramolecular religation. By attachment of EcoRI linkers, the cDNA was inserted between the phage arms and packaged in vitro. In this way, from 100 ng of ds-cDNA was obtained a gene bank which contained about $5\times10^5$ independent recombinants and 18% wild type phages.

The gene bank was screened by the method of R. A. Young and R. W. Davis, Proc. Natl. Acad. Sci. USA 80 (1983) 1194–1198, but with the modification that horseradish peroxidase was coupled to protein A, and 4-chloro-1-naphthol was used as detection system, employing the monospecific rabbit antibodies described above. In this "immunoscreening", the colonies present on nitro-cellulose filters are carefully lysed, incubated with the monospecific rabbit antibodies described above and, after removal of unbound reactants, positive plaques are detected using the modified detection system mentioned.

8 positive signals were obtained from 150,000 plaques examined. One clone with an insertion of about 300 bases was selected for further characterization; it was called BB 8.

The E. coli strain Y 1089 was infected with the recombinant phage, and the synthesis of the β-galactosidase protein was induced by addition of iso-propylthiogalactoside (IPTG). This resulted in formation of a fusion protein which is distinctly larger than galactosidase (118 kd). It is found neither in uninfected cells nor in infected but non-induced cells. Both human HCMV-positive sera and the rabbit anti-pp 150 serum reacted only with this protein in BB 8-infected, induced cells, but they did not recognize proteins either in uninfected or in non-induced infected cells. Thus, it is evident that the recombinant clone BB 8 synthesizes a fusion protein with a HCMV protein fraction.

The fusion protein from BB 8 was used to immunize a rabbit, and the antiserum was used to carry out Western Blot analyses with HCMV proteins. Only the pp 150 reacted.

The cDNA insertion of 300 bp was now used to locate the gene for pp 150 in the virus genome: for this purpose, the cDNA insertion of 300 bp was hybridized with 8 cosmid clones which encompass the entire genome of HCMV (B. Fleckenstein et al., Gene 18 (1982) 39–46). The cosmids pCM 1015 and pCM 1017, which contain the HindIII J, N and Y fragments with overlaps, hybridized with the cDNA. More detailed Southern blot analysis of this region localized the HCMV DNA fragment on a 1.5 kb EcoRI-PstI fragment (FIG. 1) which is located in the EcoRI Y fragment, specifically adjacent to the C fragment.

The cDNA of clone BB 8 was sequenced (Sanger's method). FIG. 1. It was possible, by comparison with the viral DNA sequence in this genomic region, to assign unambiguously to a long open reading frame FIG. 1. Northern blot analyses with "late" RNA and $^{32}$P-labelled DNA of the clone BB 8 (recloned in M13) produced an abundant transcript of 6.2 kb.

Northern blot analyses with variously cloned viral DNA fragments from the HindIII J and N fragment produced various size classes of "late" RNA. The strongest signal was produced by a RNA in the 6.2 kb size class.

Of all the structural proteins investigated, pp 150 was most reliably recognized by human HCMV-positive sera in Western blot analyses. In these there were reactions both with IgM-positive and with IgG-positive sera from a very wide variety of patients, for example children with congenital infections, AIDS patients as well as symptomatic and asymptomatic people.

Since it would be possible only with great technical elaboration to isolate pp 150 in the amounts necessary for diagnostic aids, the manner of preparation by gene manipulation according to the invention is especially advantageous. It has emerged that antigenic activity is shown not only by products expressed by eukaryotic cells but also by bacterial expression products. Since bacteria do not produce phosphoproteins, it could not have been expected that HCMV pp 150, or parts thereof, produced by bacteria also has strong immunogenic activity. However, it emerged that such proteins are also just as unambiguously recognized by appropriate sera as is authentic pp 150.

Thus, it is possible according to the invention to use pp 150, or immunogenic parts thereof, which has been prepared in prokaryotic or eukaryotic cells, for example yeast cells, human or animal cells, as a reagent for detecting HCMV antibodies, for example in an ELISA.

EXAMPLE

The XhoII-PstI fragment (see FIG. 1) which is located inside the HCMV EcoRI Y fragment and thus codes for parts of pp 150 was ligated in the expression vector pBD 2 (M. Br öker. Gene Anal. Techn. 3 (1986) 53–57) after the vector had been cleaved with BamHI and PstI.

Transformation of the resulting hybrid plasmid into *E. coli* BMH 71-18 was followed by isolation of clones whose plasmid DNA had the expected restriction pattern. After induction of the lac promoter with isopropyl-β-D-thiogalactopyranoside (IPTG) the clones expressed large amounts of a fusion protein having a pp 150 fraction.

The new plasmid which codes for this β-galactosidase-pp 150 fusion protein is called pXP1 hereinafter. The fusion protein coded for by pXP1 was isolated from *E. coli* cells which contain the vector pXP1 after induction with IPTG, and was used for immunizing rabbits. Serum obtained after three immunizations reacted in Western blot analyses with protein bands of about 150.000 d from HCMV-infected cell extracts but not with control extracts. Thus, antibodies raised against the pp 150 synthesized by bacteria are able to recognize authentic pp 150. In addition, it was possible to use the anti-pXP1 serum to detect HCMV by immunofluorescence only two or three days after infection of cell cultures, whereas the cytopathic effect is not detectable until ten to fourteen days have elapsed. Thus, a serum obtained using pp 150 prepared by recombination can be used as a diagnostic agent.

We claim:

1. An immunogenic peptide of a structural phosphoprotein with a molecular weight of approximately 150 kD (pp150) encoded by the XhoII-PstI DNA fragment having the nucleic acid sequence identified in FIG. 1.

2. A DNA fragment having a nucleotide sequence which encodes the amino acid sequence of the immunogenic peptide of pp 150, wherein the immunogenic peptide of pp 150 is encoded by the DNA sequence:

GATCC GCGTTTCACC GACACGCTGG TGGACAT-
CAC GGATACCGAG ACGAGCGCCA AACCGC-
CCGT CACCACCGCG TACAAGTTCG AGCAAC-
CGAC GTTGACGTTC GGCGCCGGAG
TTAACGTTCC TGCTGGCGCC GGCGCTGCCA
TCCTCACGCC GACGCCTGTC AATCCTTCCA
CGGCCCCCGC TCCGGCCCCG ACACCTACCT
TCGCGGGTAC CCAAACCCCG GTCAACGGTA
ACTCGCCCTG GGCTCCGACG GCGCCGTTGC
CCGGGGATAT GAACCCCGCC AACTGGCCGC
GCGAACGCGC GTGGGCCCTC AAGAATCCTC
ACCTGGCTTA CAATCCCTTC AGGATGCCTA
CGACTTCCAC GGCTTCTCAA AACACCGTGT
CCACCACCCC TCGGAGGCCG TCGACTCCAC
GCGCCGCGGT GACACAAACA GCGTCTCGGG
ACGCCGCTGA TGAGGTTTGG GCTTTAAGGG
ACCAAACTGC A.

3. An expression vector comprising the DNA fragment of claim 2, wherein said expression vector is pBD 2.

* * * * *